US008893643B2

(12) United States Patent
Setoguchi et al.

(10) Patent No.: US 8,893,643 B2
(45) Date of Patent: Nov. 25, 2014

(54) COATING APPARATUS AND LIQUID SUBSTANCE COATING METHOD

(75) Inventors: Yuuji Setoguchi, Shunan (JP); Tomonori Inoue, Shunan (JP)

(73) Assignee: Sekisui Medical Co., Ltd., Tokyo (JP)

( * ) Notice: Subject to any disclaimer, the term of this patent is extended or adjusted under 35 U.S.C. 154(b) by 125 days.

(21) Appl. No.: 13/389,848

(22) PCT Filed: Aug. 10, 2010

(86) PCT No.: PCT/JP2010/063527
§ 371 (c)(1),
(2), (4) Date: Feb. 10, 2012

(87) PCT Pub. No.: WO2011/019030
PCT Pub. Date: Feb. 17, 2011

(65) Prior Publication Data

US 2012/0141672 A1 Jun. 7, 2012

(30) Foreign Application Priority Data

Aug. 11, 2009 (JP) ................................ 2009-186798

(51) Int. Cl.

| | |
|---|---|
| ***B05B 13/06*** | (2006.01) |
| ***B05C 5/00*** | (2006.01) |
| ***A61B 5/15*** | (2006.01) |
| ***B05B 7/06*** | (2006.01) |
| *B05D 7/22* | (2006.01) |
| *B01L 3/00* | (2006.01) |
| *B05D 1/02* | (2006.01) |

(52) U.S. Cl.
CPC ........... *B05B 7/066* (2013.01); *A61B 5/150274* (2013.01); *B05B 13/06* (2013.01); *B01L 2200/0684* (2013.01); *B02B 1/265* (2013.01); *B05D 7/222* (2013.01); *A61B 5/150755* (2013.01); *B01L 2300/16* (2013.01); *B01L 3/5082* (2013.01); *B05D 1/02* (2013.01); *A61B 5/15003* (2013.01); *B05D 7/227* (2013.01)
USPC ........... 118/306; 118/317; 118/504; 239/490; 239/518; 239/222.15; 427/236; 427/237

(58) Field of Classification Search
CPC ........ B05B 13/06; B05B 1/126; B05B 7/066; B05C 5/00
USPC ......... 118/306, 317, 300, 321, 323, 504, 505; 239/490, 418, 424, 518, 222–222.21, 239/752, 753, 542; 427/236, 230, 233, 237
See application file for complete search history.

(56) References Cited

U.S. PATENT DOCUMENTS

| | | | | |
|---|---|---|---|---|
| 2,520,397 | A | 8/1950 | Green | |
| 4,658,754 | A | 4/1987 | Messner et al. | |
| 2006/0278736 | A1 * | 12/2006 | Reilly et al. | .................. 239/542 |

FOREIGN PATENT DOCUMENTS

| | | | |
|---|---|---|---|
| DE | 44 40 666 | A1 | 5/1996 |
| EP | 1 048 358 | A2 | 11/2000 |

(Continued)

OTHER PUBLICATIONS

International Preliminary Report on Patentability for Application No. PCT/JP2010/063527 mailed Sep. 14, 2010.

(Continued)

*Primary Examiner* — Yewebdar Tadesse
(74) *Attorney, Agent, or Firm* — Cheng Law Group, PLLC

(57) ABSTRACT

Provided is a coating apparatus in which a liquid substance is less likely to splash around and a chemical solution can be coated on a specific region of the inside surface of a tubular container. The coating apparatus 10 includes a spraying direction changing member 12, fixed to a tip portion of a spray nozzle 4 with an inner tube 6 and an outer tube 7, for changing the direction of spray of a sol oriented outward to a direction intersecting a direction of discharge of the liquid substance from the inner tube 6.

21 Claims, 12 Drawing Sheets

(56) References Cited

FOREIGN PATENT DOCUMENTS

| | | | |
|---|---|---|---|
| JP | 3-11444 | U | 2/1991 |
| JP | 3-202166 | A | 9/1991 |
| JP | 10-305024 | A | 11/1998 |
| JP | 2007-245098 | A | 9/2007 |
| WO | WO-2008/037755 | A1 | 4/2008 |

OTHER PUBLICATIONS

Supplementary European Search Report for the Application No. EP 10 80 8213 dated Jan. 14, 2013.

International Search Report for the Application No. PCT/JP2010/063527 mailed Sep. 14, 2010.

* cited by examiner

FIG. 5
(a)
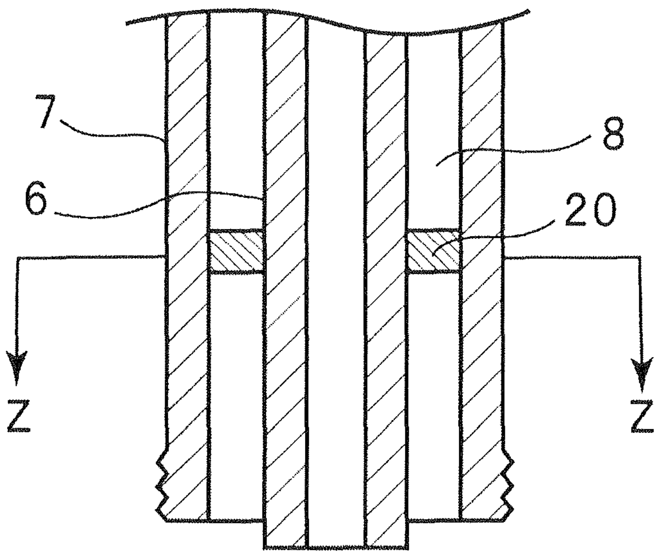
(b)
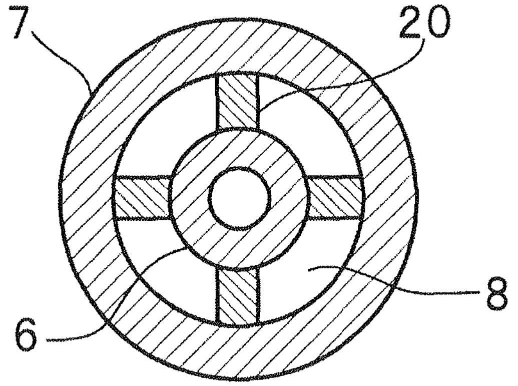

FIG. 8
(a)
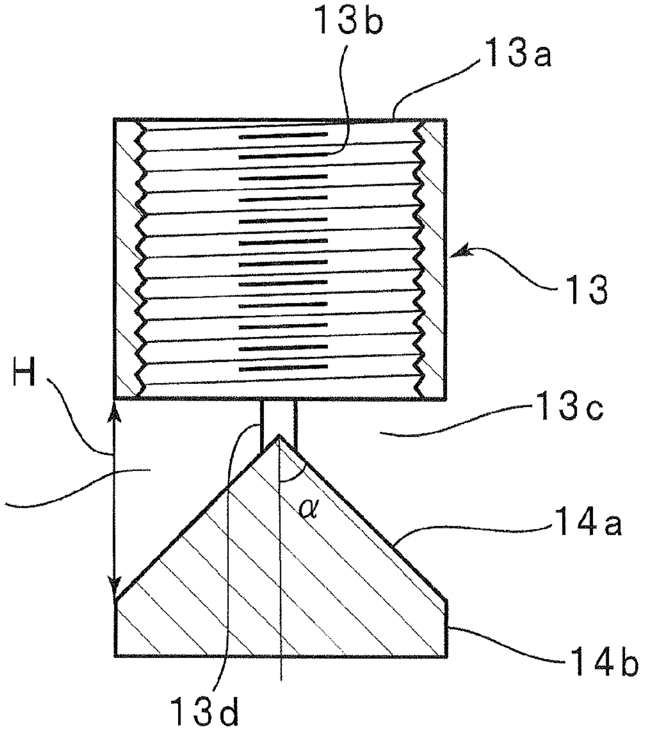
(b)
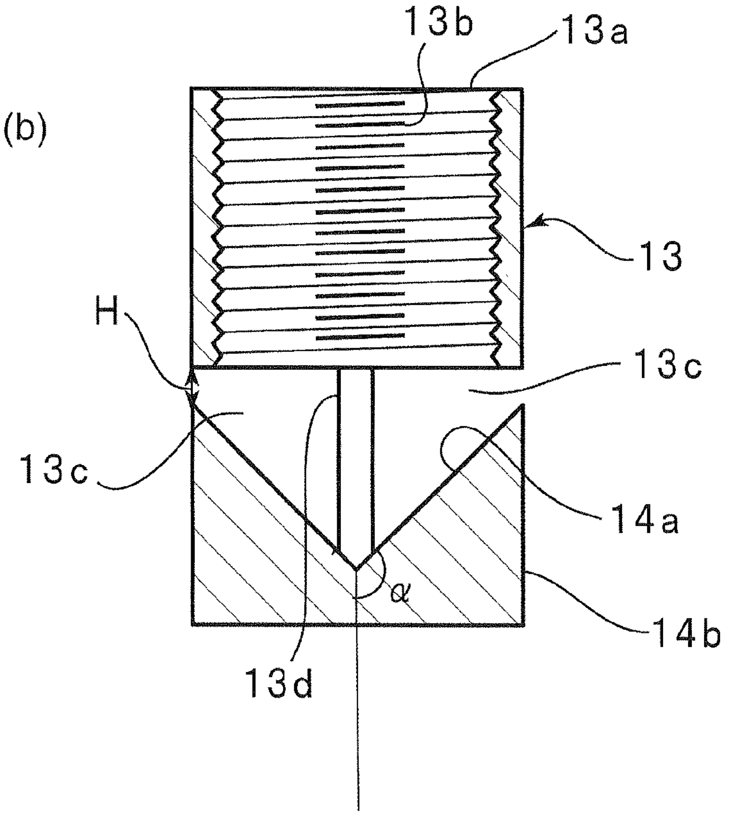

FIG. 9
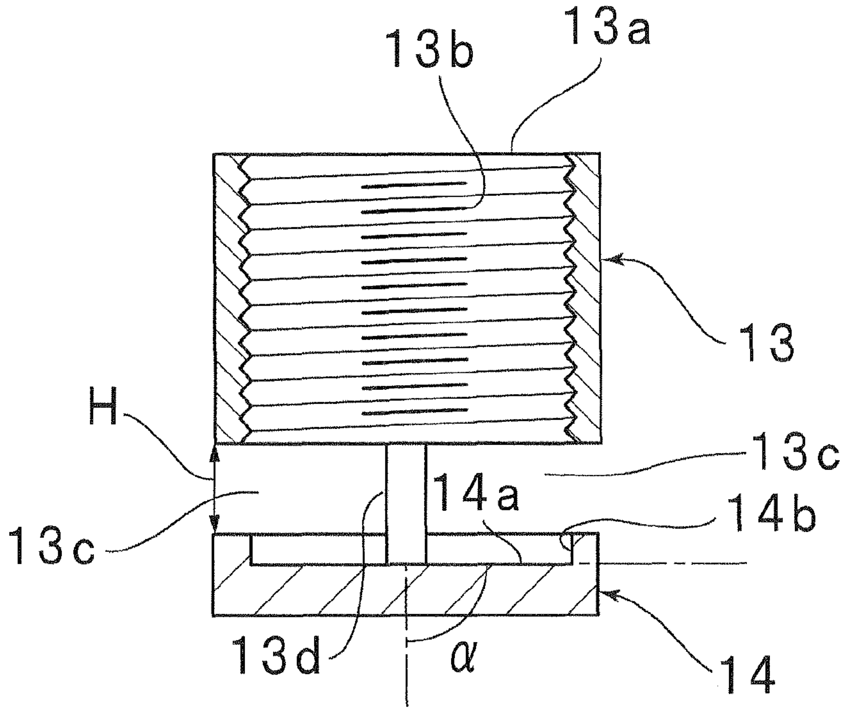
[FIG. 10]
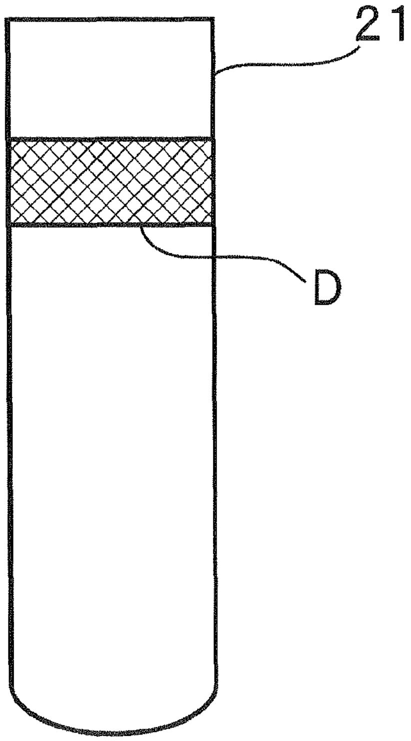

FIG. 13
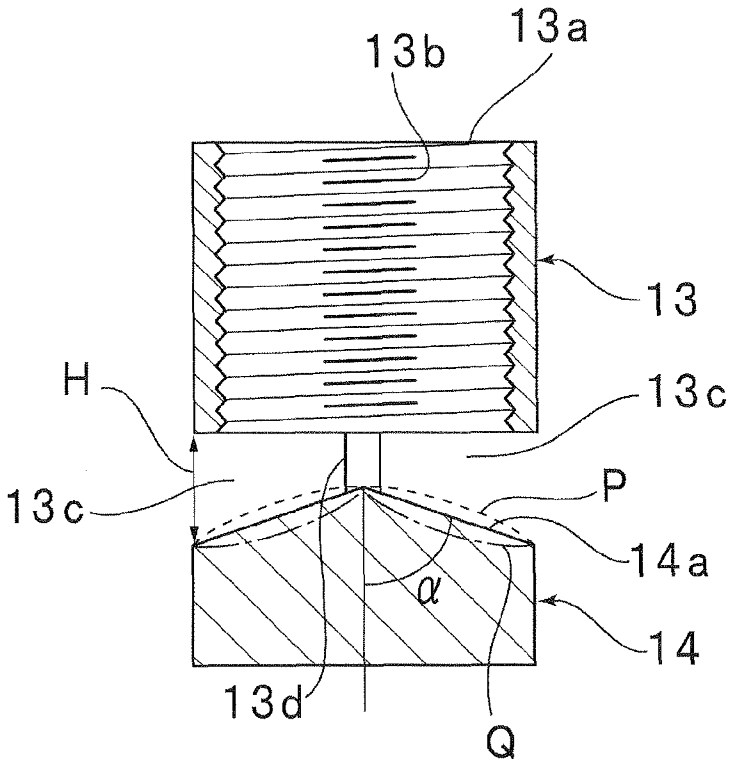
[FIG. 14]
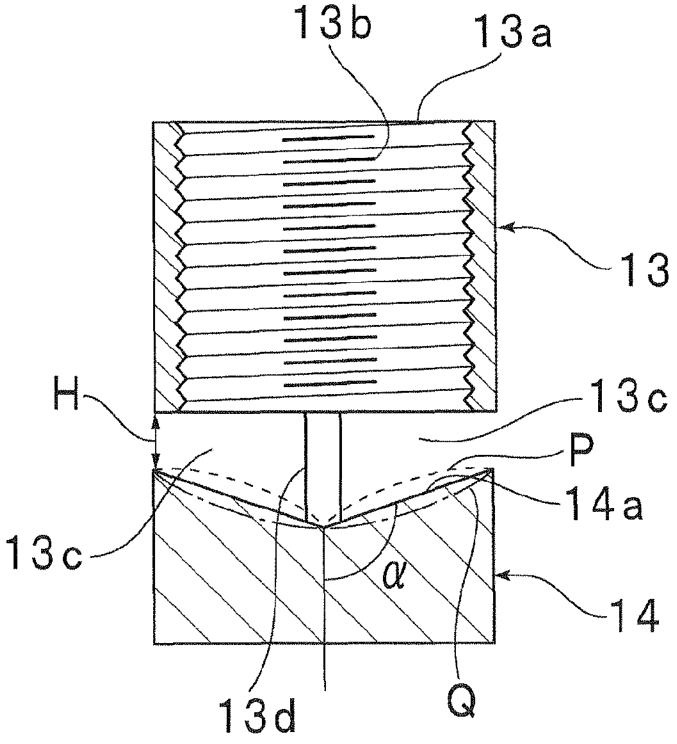

COATING APPARATUS AND LIQUID SUBSTANCE COATING METHOD

TECHNICAL FIELD

This invention relates to apparatuses for coating a liquid substance on the inside surface of a tubular container and liquid substance coating methods and more particularly relates to coating apparatuses with a spray nozzle for spraying a sol and liquid substance coating methods using the coating apparatuses.

BACKGROUND ART

For example, Patent Literature 1 below discloses a method for spraying a chemical solution through a spray nozzle in order to coat the chemical solution on substantially the entire region of the inside surface of a tubular blood testing container. The spray nozzle includes an outer tube and an inner tube inserted in the outer tube. The chemical solution is fed to the inner tube and a gas is fed to a space between the outer and inner tubes.

In use, the tip of the spray nozzle is inserted into the blood testing container, and in this state the chemical solution and gas are simultaneously supplied into the container. The chemical solution discharged from the distal end of the inner tube is turned into an aerosol by the gas, so that the chemical aerosol is sprayed from the tip of the spray nozzle. The chemical aerosol is splashed around by streams of the gas. After the start of spraying, the spray nozzle is moved up in the tubular blood testing container to coat the chemical solution on substantially the entire region of the inside surface of the blood testing container.

CITATION LIST

Patent Literature

Patent Literature 1: JP-A-H10-305024

SUMMARY OF INVENTION

Technical Problem

With the use of the spray nozzle described in Patent Literature 1, the chemical aerosol is apt to randomly splash over the surrounding area. Therefore, the chemical may splash outside of the tubular container. In addition, the spray nozzle has difficulty coating the chemical solution only on a desired specific region of the inside surface of the tubular container.

An object of the present invention is to provide a coating apparatus capable of coating a liquid substance on a specific region of the inside surface of a tubular container and provide a liquid substance coating method for coating a liquid substance on the inside surface of a tubular container using a spray nozzle, whereby the liquid substance is less likely to splash outside of the container and can be coated on a specific region of the inside surface of the tubular container.

Solution to Problem

A coating apparatus according to the present invention is a coating apparatus for coating a liquid substance on a specific region of the inside surface of a tubular container and includes: a spray nozzle including an inner tube for discharging the liquid substance and an outer tube for discharging a medium exhibiting fluidity with the inner tube inserted therein, the spray nozzle being configured to spray from a tip thereof the liquid substance discharged from the inner tube as a sol by means of the medium discharged from the outer tube; and a spraying direction changing member, fixed to the tip side of the spray nozzle, for changing a direction of spray of the sol oriented outward to a direction intersecting the direction of discharge of the liquid substance.

Preferably, the spraying direction changing member includes a cylindrical body with a hollow part extending from the tip of the spray nozzle in the direction of discharge of the liquid substance and closed at the distal end of the hollow part, and the sidewall of the cylindrical body has openings formed to pass through the sidewall in a direction intersecting the direction of discharge of the liquid substance from the inner tube. The sol is sprayed outward through the openings. In this case, since the openings pass through the sidewall in the direction intersecting the direction of discharge of the liquid substance from the inner tube, the direction of spray of the sol to be sprayed outward through the openings is restricted. Therefore, the liquid substance can be easily coated only on the specific region of the inside surface of the tubular container.

The spraying direction changing member more preferably further includes a bounce part provided on the side beyond the openings of and at the distal end of the cylindrical body and having a bounce surface for bouncing off the sol. In this case, the sol having reached the bounce part is bounced back by the bounce part. Therefore, by adjusting the bounce direction, the liquid substance can be easily coated only on the specific region of the inside surface of the tubular container.

The bounce surface may be a flat surface or may be a convex surface projecting toward the spray nozzle or a concave surface whose deepest part is located on the side opposite to the spray nozzle.

The bounce surface is preferably a surface which, when a first straight line beginning at an arbitrary point and extending in one direction is rotated 360 degrees around an axis of rotation which is a second straight line beginning at the arbitrary point and not parallel with the first straight line, is formed by the first straight line. In other words, the bounce part preferably has a flat surface or a conical surface as the surface formed by the first straight line rotated in the above manner. In this case, the bounce direction can be easily adjusted, whereby the liquid substance can be easily coated only on the specific region of the inside surface of the tubular container.

The angle formed between the first straight line and the second straight line is preferably within the range of 45 to 135 degrees. In this case, as compared to cases where the angle is out of the above range, the sol can be easily collected to a region of the inside surface of the tubular container which faces the openings. Thus, the liquid substance can be more easily coated on the specific region of the inside surface of the tubular container.

The angle formed between the first straight line and the second straight line is more preferably 90 degrees. In this case, the bounce part can be easily formed. In addition, the region where the sol is to be collected can be easily adjusted, whereby the sol can be more easily coated on the specific region of the inside surface of the tubular container. More preferably, the first straight line is provided to be orthogonal to the direction of discharge of the liquid substance. In this case, the second straight line coincides with the direction of discharge of the liquid substance.

It is preferred that the inner tube have a distal end opening in the shape of a circle and the second straight line be a straight line extending from the center of the circle in the direction of discharge of the liquid substance.

Preferably, the coating apparatus according to the present invention further includes a second bounce part provided on the tip side of the spray nozzle and outward of a part of the spray nozzle from which the medium exhibiting fluidity is discharged, the second bounce part being opposed to the bounce part of the spraying direction changing member, wherein the second bounce part has a bounce surface formed to re-bounce the sol bounced back from the bounce surface of the bounce part of the spraying direction changing member and spray the sol outward.

The second bounce part preferably has a surface which, when a first straight line beginning at an arbitrary point and extending in one direction is rotated 360 degrees around an axis of rotation which is a second straight line beginning at the arbitrary point and having an angle of 45 to 135 degrees made with the first straight line, is formed by the first straight line. In this case, the sol can be more effectively bounced at the second bounce part toward the specific region of the inside surface of the tubular container.

The medium exhibiting fluidity is preferably a gas. Thus, the liquid substance can be sprayed as an aerosol from the spray nozzle. The sol sprayed from the spray nozzle is preferably aerosol.

The coating apparatus according to the present invention can be used for various applications for coating a liquid substance on the inside surface of a tubular container; however, the tubular container is preferably a blood testing container.

A liquid substance coating method according to the present invention is a method for coating a liquid substance on a specific region of the inside surface of a tubular container and includes the steps of: positioning the coating apparatus configured in accordance with the present invention in the tubular container so that a direction of spray of a sol oriented outward is turned toward the specific region of the tubular container; and coating the sol on the specific region of the container by discharging the liquid substance from the inner tube of the spray nozzle of the coating apparatus and a medium exhibiting fluidity from the outer tube of the spray nozzle to thereby spray the sol from the spray nozzle and changing the direction of spray of the sol oriented outward to a direction intersecting a direction of discharge of the liquid substance from the inner tube of the spray nozzle by means of the spraying direction changing member of the coating apparatus.

Preferably, the spraying direction changing member includes a cylindrical body with a hollow part extending from the tip of the spray nozzle in the direction of discharge of the liquid substance and closed at the distal end of the hollow part, and the sidewall of the cylindrical body has openings formed to pass through the sidewall in a direction intersecting the direction of discharge of the liquid substance from the inner tube. The sol is sprayed outward through the openings. In this case, the sol is sprayed through the openings formed to pass through the sidewall in the direction intersecting the direction of discharge of the liquid substance from the inner tube. Therefore, the direction of spray of the sol is restricted, whereby the liquid substance can be easily coated only on the specific region of the inside surface of the tubular container.

Preferably, the medium exhibiting fluidity is a gas, the sol sprayed from the spray nozzle is aerosol, and the tubular container is a blood testing container.

Advantageous Effects of Invention

In the coating apparatus according to the present invention, since the direction of spray of sol sprayed from the spray nozzle tip, having been oriented outward, is changed to a direction intersecting the direction of discharge of the liquid substance by means of the spraying direction changing member, the direction of spray can be set so that the liquid substance can be deposited only on a specific region of the inside surface of a tubular container. Therefore, with the use of the coating apparatus according to the present invention, the liquid substance can be coated on the specific region of the inside surface of the tubular container. In addition, the direction of spray of the sol oriented outward is restricted by the spraying direction changing member. Therefore, it can be avoided that the sol randomly splashes away. Moreover, by adjusting the direction of spray, the sol can be less likely to splash outside of the tubular container.

Since the liquid substance coating method according to the present invention uses the coating apparatus configured in accordance with the present invention, a liquid substance can be coated on a specific region of the inside surface of a tubular container without addition of any complicated step. In addition, since the sol is sprayed only on the specific region of the inside surface of the tubular container, the sol can be less likely to splash outside of the tubular container and the liquid substance can be efficiently coated.

BRIEF DESCRIPTION OF DRAWINGS

FIG. 5(*a*) is a schematic partly cutaway cross-sectional front view of the spray nozzle for use in the coating apparatus according to the one embodiment of the present invention for illustrating a connecting part between the outer and inner tubes, and FIG. 5(*b*) is a cross-sectional view taken along the line Z-Z in FIG. 5(*a*).

FIGS. 8(*a*) and 8(*b*) are cross-sectional front views schematically showing respective spraying direction changing members used in Examples 4 and 5.

FIG. 9 is a cross-sectional front view schematically showing a spraying direction changing member used in Example 1.

FIG. 10 is a cross-sectional front view schematically showing a state that a blood coagulation promoter is coated on the inside surface of a tubular container in Example 1.

FIG. 13 is a cross-sectional front view schematically showing the relationship between a bounce surface of a spraying direction changing member for use in a coating apparatus according to an embodiment of the present invention and the angle α.

FIG. 14 is a cross-sectional front view schematically showing the relationship between a bounce surface of a spraying direction changing member for use in a coating apparatus according to another embodiment of the present invention and the angle α.

DESCRIPTION OF EMBODIMENTS

Figure 1:
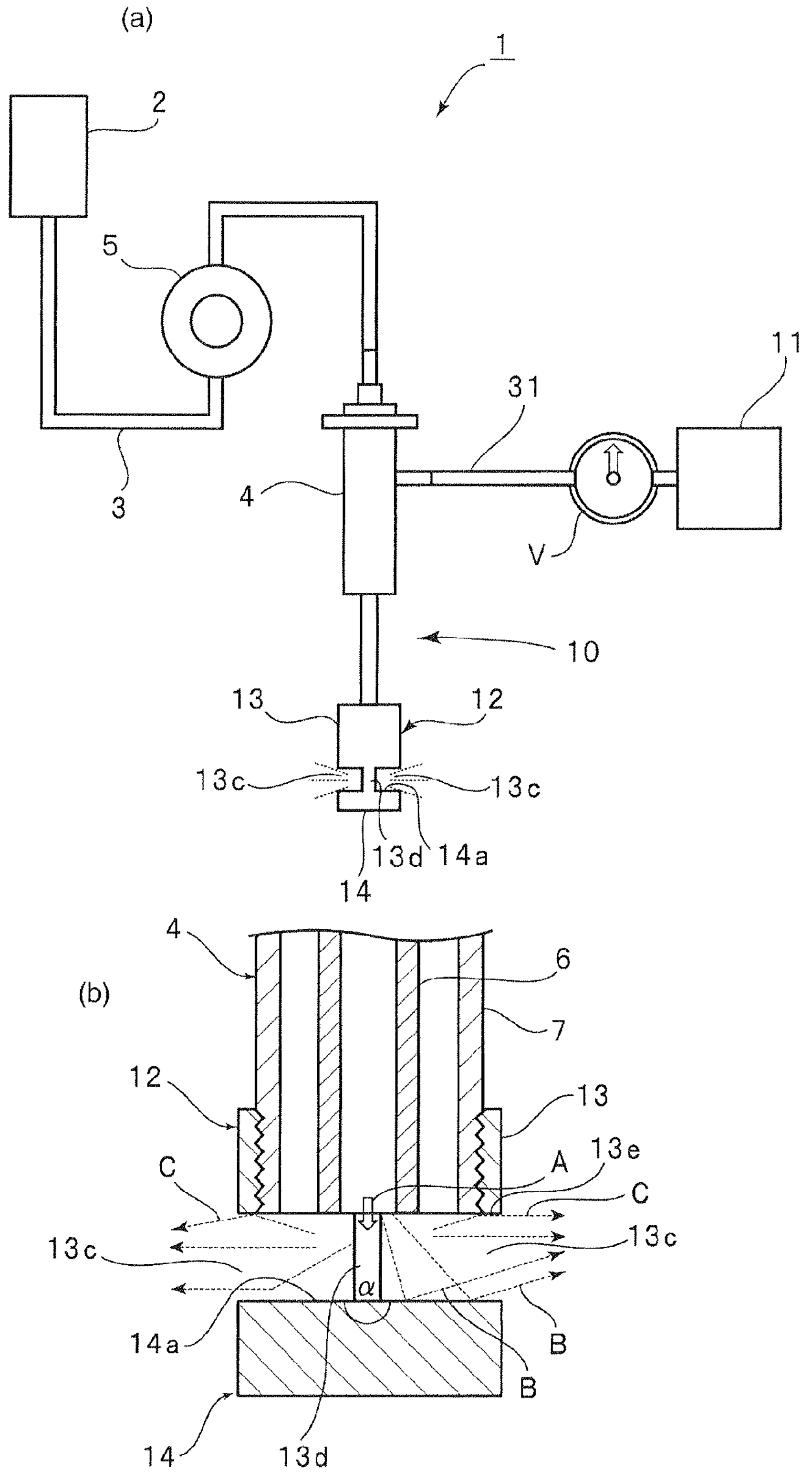
FIGS. 1(*a*) and 1(*b*) area schematic block diagram of a system including a coating apparatus according to one embodiment of the present invention and a partly cutaway cross-sectional front view of an essential part of the coating apparatus, respectively.

Hereinafter, the present invention will become apparent by explaining specific embodiments of the present invention with reference to the drawings. Note that components in the drawings are schematically illustrated and the dimension ratio between them may be different from the actual dimension ratio.

The following embodiments describe a coating apparatus in which a chemical solution is used as a liquid substance, a blood testing container is used as a tubular container, and a gas is used as a medium exhibiting fluidity, and a method for coating a chemical solution using the coating apparatus. In the present invention, however, the type of liquid substance is not limited to chemical solutions but may include various liquid substances, and the type of tubular container is not limited to the blood testing container but may include various tubular containers.

Furthermore, in the present invention, the type of medium exhibiting fluidity is not limited to gases, but liquids or other fluids may be used. When gas is used as a medium exhibiting fluidity, a sol sprayed from the spray nozzle takes the form of an aerosol.

FIG. 1(*a*) is a schematic block diagram of a system including a coating apparatus according to an embodiment of the present invention. FIG. 1(*b*) is a partly cutaway cross-sectional front view schematically showing an essential part of the coating apparatus shown in FIG. 1(*a*). In FIG. 1 and the figures to follow, for convenience of graphical representation and description, components, such as a spray nozzle and a spraying direction changing member are illustrated by appropriately changing their sizes from the actual sizes.

A system 1 includes a coating apparatus 10 and further includes a chemical solution tank 2, a pump 5, and other components. The coating apparatus 10 includes a spray nozzle 4, a spraying direction changing member 12, and other components. A chemical solution to be coated is contained in the chemical solution tank 2.

The chemical solution tank 2 is connected through a pipe 3 to the spray nozzle 4. The pump 5 is connected to an intermediate point on the pipe 3 in order to deliver the chemical solution. The chemical solution tank 2, the pipe 3, and the pump 5 can be formed from appropriate materials and structures conventionally used to coat a chemical solution by means of a spray nozzle.

Figure 2:
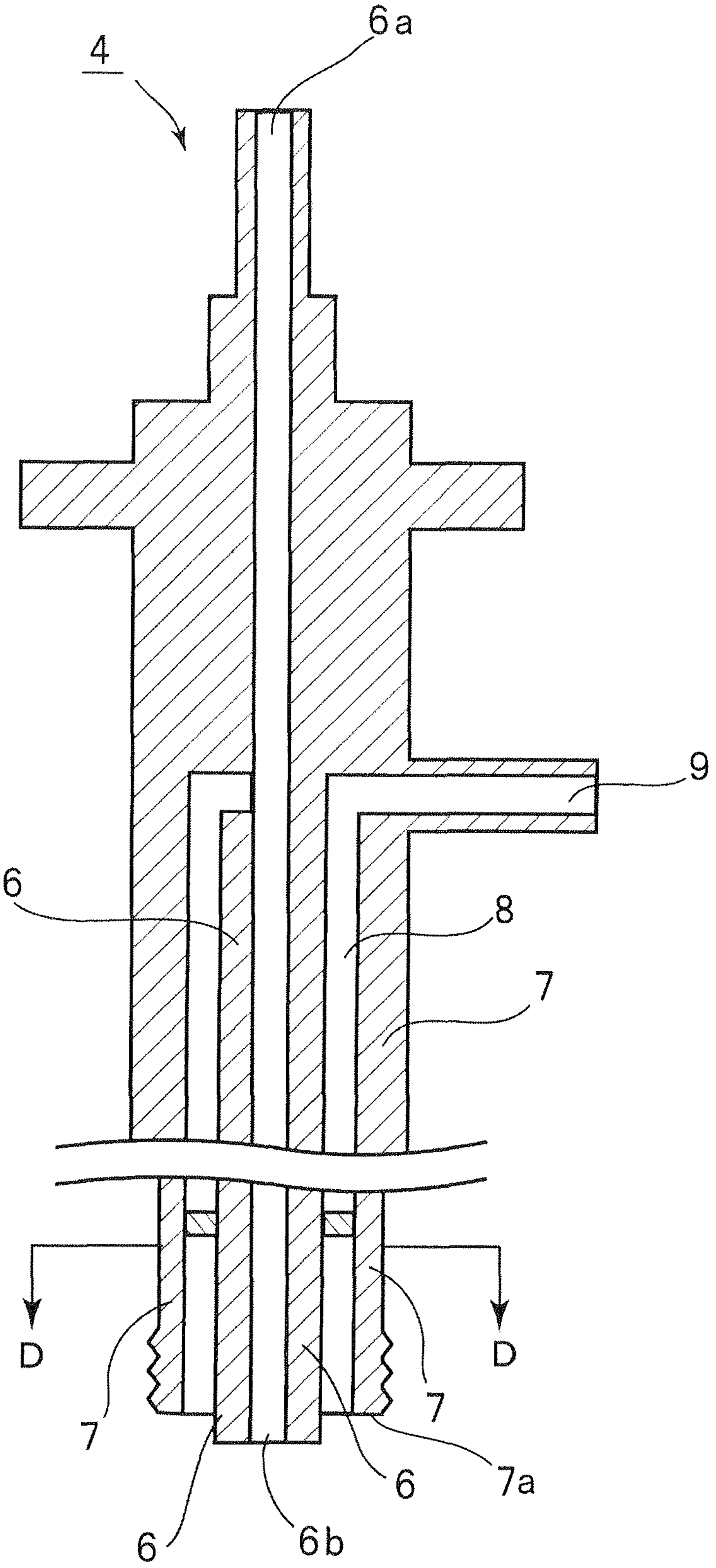
FIG. 2 is a cross-sectional front view schematically showing a spray nozzle for use in the one embodiment of the coating apparatus according to the present invention.

As schematically shown in a cross-sectional front view in FIG. 2, the spray nozzle 4 includes an inner tube 6 and an outer tube 7 in which the inner tube 6 is inserted. The inner tube 6 and the outer tube 7 are integrally formed at their upstream sides in FIG. 2 but may be formed of separate members and partly connected to each other. An opening 6*a* of the inner tube is located on the upstream side of the spray nozzle 4. The pipe 3 is connected to the opening 6*a*, so that the chemical solution is fed to the inside of the inner tube 6. The inner tube 6 has a discharge opening 6*b* formed at its distal end (on the downstream side) to discharge the chemical solution therethrough. In other words, the inner tube 6 is a member having a chemical solution channel connecting the opening 6*a* and the discharge opening 6*b*. The inner tube 6 has a cylindrical hollow shape in this embodiment, but it may have another shape, such as a prismatic hollow shape. Since in this embodiment the inner tube 6 is cylindrical, the shapes of the end openings of the inner tube 6 are circular.

Figure 3:
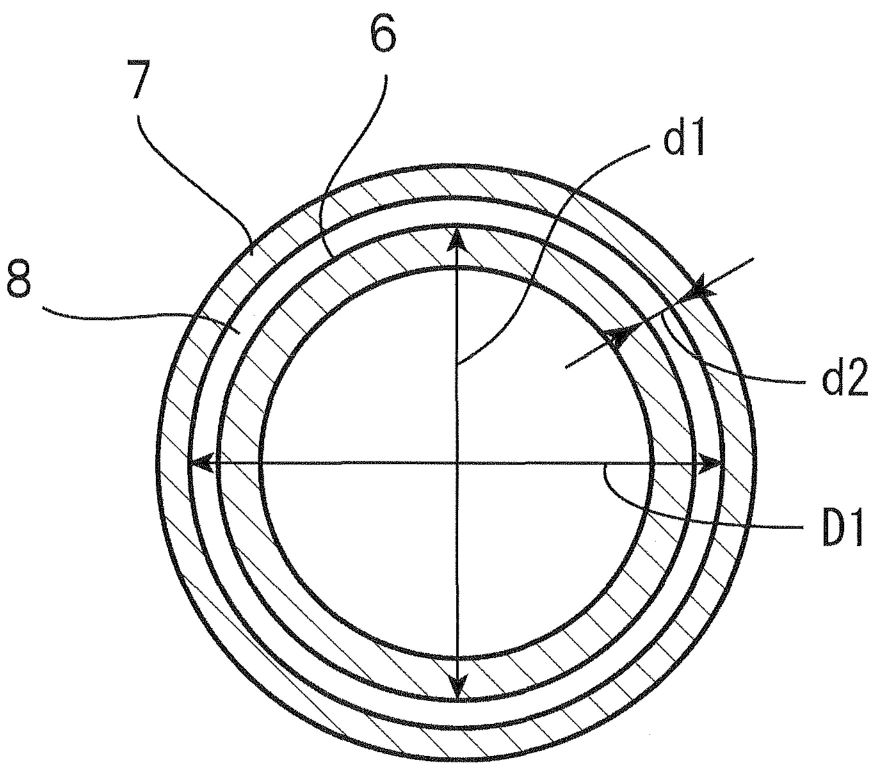
FIG. 3 is a schematic cross-sectional view of the spray nozzle for use in the coating apparatus according to the one embodiment of the present invention taken along the line D-D in FIG. 2 and is for illustrating the relationship between the sizes of the inner and outer tubes.

The outer tube 7 is provided to feed a gas serving as a pressure medium, such as a compressed gas, to a space between the outside wall of the inner tube 6 and the inside wall of the outer tube 7. In this embodiment, the outer tube 7 has a cylindrical hollow shape. Thus, the space 8 between the outside wall of the inner tube 6 and the inside wall of the outer tube 7 is a space having a substantially circular transverse section as shown in FIG. 3. The space 8 communicates on the upstream side with an opening 9 (see FIG. 2) provided laterally of the outer tube 7.

FIG. 5(*a*) is a partly cutaway cross-sectional front view schematically showing a part of a centering structure for allowing the inner tube 6 to be positioned near the center of the outer tube 7, and FIG. 5(*b*) is a cross-sectional view taken along the line Z-Z in FIG. 5(*a*). The outside wall of the inner tube 6 is in contact with the centering structure 20 fixed to the inside wall of the outer tube 7, so that the inner tube 6 can be positioned near the center of the outer tube 7. By controlling the size of the centering structure 20, the inner tube 6 can be easily positioned in the center of the outer tube 7.

However, the centering structure 20 for positioning the inner tube 6 near the center of the outer tube 7 is not limited to this configuration. Furthermore, the centering structure 20 may be fixed to either the outside surface of the inner tube 6 or the inside surface of the outer tube 7.

As shown in FIG. 1(*a*), a pipe 31 is connected to the opening 9 located laterally of the outer tube 7. The pipe 31 is connected to a compressor 11 for feeding a gas, such as a compressed gas, to the space 8. Connected to an intermediate point on the pipe 31 is a valve V for adjusting the flow rate of the gas. The pipe 31, the compressor 11, and the valve V can be formed of an appropriate compressor, pipe, and valve of types conventionally used in coating a chemical solution using a spray.

The gas is fed from the compressor 11 through the pipe 31 to the space 8, and at the tip of the spray nozzle 4 the chemical solution discharged from the inner tube 6 is sheared by the gas discharged from the space 8 to turn into a chemical aerosol.

FIG. 3 is a cross-sectional view taken along the line D-D in FIG. 2. In relation to the inner tube 6 and the outer tube 7, it is desired that when the outside diameter of the inner tube 6 is represented by d1 and the inside diameter of the outer tube 7 is represented by D1, the thickness of the space 8, namely, d2 the distance between the inside wall of the outer tube 7 and the outside wall of the inner tube 6, be within the range of 25% to 75% of the difference ΔD between D1 and d1. When d2 is within this range, a chemical aerosol can be uniformly and more reliably formed. However, the magnitude of d2 is not limited to this range.

In the coating apparatus 10, the spraying direction changing member 12 is fixed to the tip of the spray nozzle 4. As shown in FIGS. 1(*b*) and 4, the spraying direction changing member 12 includes a cylindrical body 13.

Figure 4:
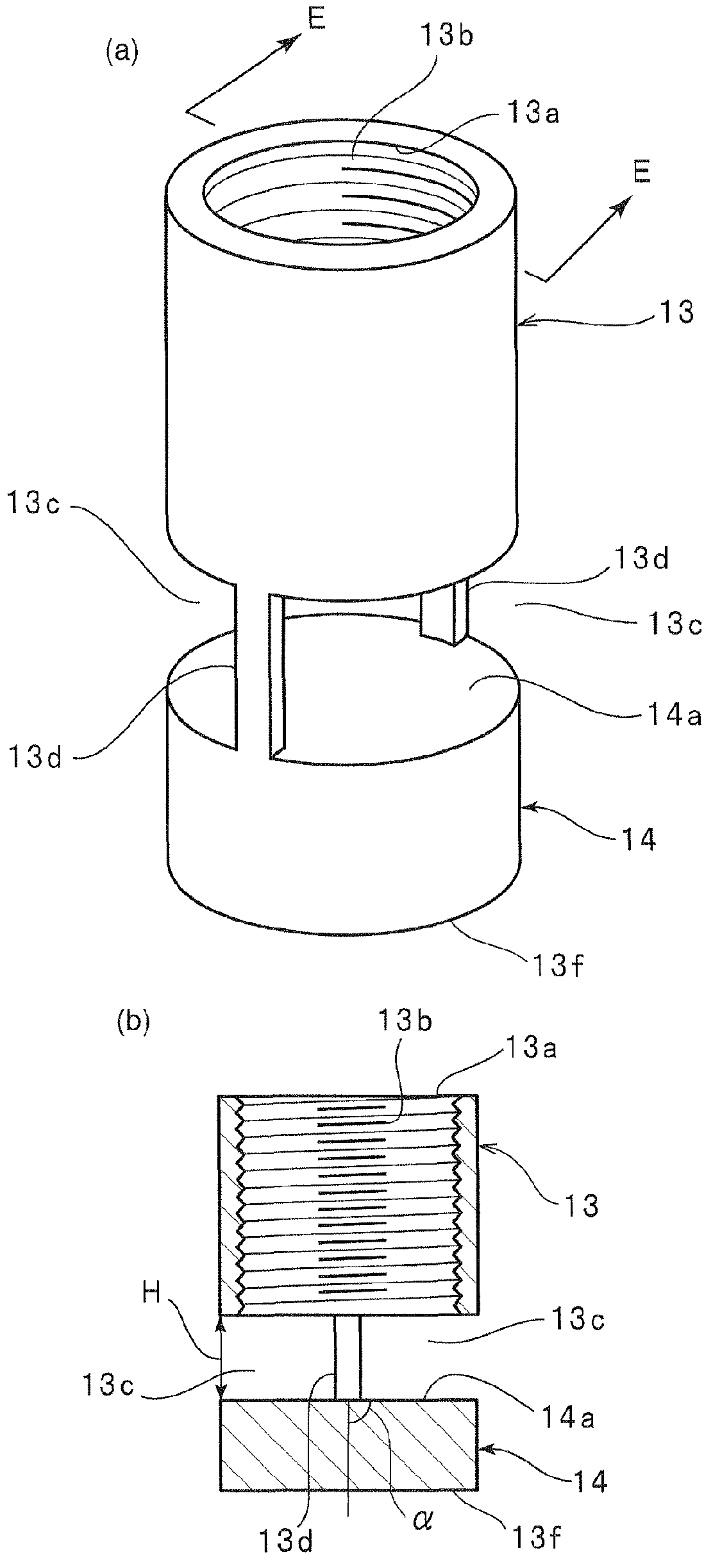
FIG. 4(*a*) is a perspective view schematically showing a spraying direction changing member for use in the coating apparatus according to the one embodiment of the present invention, and FIG. 4(*b*) is a cross-sectional view taken along the line E-E in FIG. 4(*a*).

As shown in FIG. 4, the cylindrical body 13 has an opening 13*a* at the proximal end. Internal threads 13*b* are formed on the inner periphery of the cylindrical body 13 in the vicinity of the opening 13*a*. External threads are formed on the outer periphery of a distal portion of the outer tube 7 of the spray nozzle 4. By screwing the distal portion of the outer tube 7 having the external threads onto the portion of the cylindrical body 13 having the internal threads 13*b*, the spraying direction changing member 12 is fixed to the spray nozzle 4.

As used herein, the proximal end of the cylindrical body 13 is referred to as an end closer to the spray nozzle 4 and the distal end thereof is referred to as an end opposite to the proximal end. Herein, the cylindrical body 13 includes a bounce part 14 described later. Therefore, the distal end 13*f* of the cylindrical body 13 corresponds to the underside of the later-described bounce part 14 as viewed in FIG. 4. This means that the cylindrical body 13 is closed at its distal end by the bounce part 14.

However, the structure for fixing the spraying direction changing member 12 to the tip side of the spray nozzle 4 is not limited to the above. Other appropriate fixing methods, for example, fixing with a bonding material such as an adhesive, may also be used. When fixed by screwing as in this embodiment, the spraying direction changing member 12 can be freely attached to and removed from the spray nozzle 4. Thus, the spraying direction changing member 12 can be easily replaced or easily changed to any spraying direction changing member having a different shape.

A plurality of openings 13*c* and 13*c* are formed between the proximal and distal ends of the cylindrical body 13. In the cylindrical body 13, a hollow part continuing from the opening 13*a* is formed from the proximal side toward the distal side to reach the openings 13*c* and 13*c*. The openings 13*c* and 13*c* are formed by providing narrow connecting parts 13*d* and 13*d* extending from the proximal side toward the distal side. The opening 13*c* has a substantially rectangular shape, looking at the cylindrical body 13 from the side. However, the shape of the opening 13*c* is not limited to such a substantially rectangular shape. The plurality of openings 13*c* and 13*c* are distributed circumferentially of the cylindrical body 13.

The connecting parts 13*d* and 13*d* have their outside surfaces forming portions of the outer periphery of the cylindrical body 13 and have an appropriate thickness. In this embodiment, the thickness of the connecting parts 13*d* and 13*d* is selected to be equivalent to the thickness of the portion of the cylindrical body 13 formed with the opening 13*a*. Thus, the inside surfaces of the connecting parts 13*d* and 13*d* are formed to continue to the inner periphery of the portion of the cylindrical body 13 formed with the hollow part continuing from the opening 13*a*. However, the thickness of the connecting parts 13*d* and 13*d* may be smaller or larger than that of the portion of the cylindrical body 13 where the opening 13*a* is formed.

The openings 13*c* and 13*c* have substantially rectangular shapes as viewed from the side and have substantially semicircular shapes in plan view. As shown in FIGS. 4(*a*) and 4(*b*), in this embodiment, the two openings 13*c* and 13*c* are arranged circumferentially of the cylindrical body 13. However, three or more openings may be circumferentially arranged. In such cases, two or more connecting parts will be provided.

The connecting parts 13*d* and 13*d* each have the shape of a vertically extending narrow strip, and their width is much smaller than the length of the openings 13*c* and 13*c* along the circumference of the cylindrical body 13. In other words, at the height of the openings 13*c* and 13*c*, a major portion of the outer periphery of the cylindrical body 13 is occupied by the plurality of openings 13*c* and 13*c*. The reason for this is that the openings 13*c* and 13*c* need a large area because they are parts for spraying the chemical aerosol outward therethrough and that the connecting parts 13*d* and 13*d* are nothing more than parts simply connecting the proximal and distal ends of the cylindrical body 13. Therefore, so long as the openings 13*c* and 13*c* and connecting parts 13*d* and 13*d* perform such functions, the shape of the openings 13*c* and 13*c* is not particularly limited and the shape of the connecting parts 13*d* and 13*d* is also not particularly limited.

The length of the connecting parts 13*d* and 13*d* determines the vertical dimension of the openings 13*c* as viewed in FIG. 4(*a*). Therefore, the length of the connecting parts 13*d* and 13*d* is selected depending on the width of coating of the chemical aerosol.

The chemical solution serving as a liquid substance is discharged from the inner tube 6 in a direction shown in the arrow A in FIG. 1(*b*), i.e., in a direction connecting the proximal and distal ends of the cylindrical body 13. In contrast, the openings 13*c* and 13*c* each correspond to a shape obtained by partly cutting away the sidewall of the cylindrical body 13, and therefore they have a shape passing through part of the cylindrical body 13 and opening in a direction intersecting the direction shown in the arrow A.

As shown in FIGS. 4(*a*) and 4(*b*), the bounce part 14 is provided distal to the connecting parts 13*d* and 13*d*. The bounce part 14 has a bounce surface 14*a* at the proximal end. This bounce surface 14*a* is a substantially circular, flat surface and portions of its peripheral edge form distal edges of the openings 13*c* and 13*c*.

The bounce surface 14*a*, as shown in FIG. 1(*b*), bounces off the chemical aerosol sprayed downward, i.e., in the direction of the arrow A, to change the direction of spray to a direction toward the openings 13*c*. In other words, the bounce surface 14*a* of the bounce part 14 changes the direction of spray of the chemical aerosol having hit the bounce surface 14*a* to a direction intersecting the direction of discharge of the chemical solution from the inner tube 6. In this embodiment, the intersecting direction, as shown in FIG. 1(*b*) is the direction substantially orthogonal to the direction of the arrow A, i.e., lateral. However, the intersecting direction need only intersect the direction of the arrow A and need not necessarily be orthogonal to the direction of the arrow A.

As shown in FIG. 1(*b*), in this embodiment, the bounce surface 14*a* of the bounce part 14 is a flat surface extending in a direction orthogonal to the direction of discharge of the chemical solution from the inner tube 6, i.e., to the direction indicated by the arrow A. However, the bounce surface is not limited to such a flat surface. The bounce surface is now described in more detail with reference to FIG. 6. The bounce surface is a surface which, when a first straight line L beginning at an arbitrary point O and extending in one direction is rotated 360 degrees around an axis of rotation which is a second straight line M beginning at the arbitrary point O and not parallel with the first straight line L, is formed by the first straight line L. Assuming that the point O is a point located at the center of the bounce surface and where the angle formed between the first straight line L and the second straight line M is represented by $\alpha$, the bounce surface is a convex conical surface at an angle $\alpha$ of below 90 degrees as shown in FIG. 7(*b*) and a concave conical surface at an angle $\alpha$ of above 90 degrees as shown in FIG. 7(*c*). When the angle $\alpha$ is 90 degrees, the bounce surface is a flat surface as shown in FIGS.

4(*b*) and 7(*a*). Then, when the second straight line M coincides with the direction of discharge of the liquid substance (the direction indicated by the arrow A in FIG. 1), the bounce surface is a flat surface orthogonal to the direction of discharge of the liquid substance as shown in FIG. 4(*a*). This embodiment shown in FIGS. 1 and 4 corresponds to the case where the angle α is 90 degrees and the second straight line M coincides with the direction indicated by the arrow A.

The angle α formed between the first straight line L and the second straight line M is preferably within the range of 45 to 135 degrees. Within this range, the liquid substance, such as a chemical solution, can be coated more collectively on a specific region of the inside surface of the tubular container. By way of example, FIG. 13 shows a spraying direction changing member 12 in which the angle α is 80 degrees. Furthermore, FIG. 14 shows a spraying direction changing member 12 in which α is 100 degrees.

The bounce surface may be of curved surface shape as shown in the broken line P or the dash-single-dot line Q in FIGS. 13 and 14. Specifically, the bounce surface 14*a* may be a curved surface obtained by rotating, instead of the first straight line L in FIG. 6, a curved line extending from the point O as defined above to the outer peripheral edge of the bounce surface and projecting upward 360 degrees around the straight line M as an axis of rotation. Conversely, as shown in the dash-single-dot line Q in FIGS. 13 and 14, the bounce surface 14*a* may be a curved surface having a concave curvature from the center to outer peripheral edge of the bounce surface. In other words, the bounce surface 14*a* may be formed of a curved surface obtained by rotating, instead of the first straight line L in FIG. 6, a curved line extending from the point O to the outer peripheral edge of the bounce surface and projecting downward 360 degrees around the straight line M as an axis of rotation.

Alternatively, the bounce surface 14*a* may be a surface formed by rotating a curved line consisting of an appropriate combination of a concave surface and a convex surface between the center and the outer peripheral edge of the bounce surface in the above manner, so long as it does not have an adverse effect on the chemical coating performance.

The second straight line M is preferably a straight line extending from substantially the center of the distal end opening of the inner tube in the direction of discharge of the liquid substance. When the shape of the distal end opening of the inner tube is a circle, the second straight line M is preferably a straight line extending from the center of the circle in the direction of discharge of the liquid substance. In this case, the bounce surface of the bounce part is formed symmetrically with respect to the center of the direction of discharge of the liquid substance, so that the liquid substance can be coated uniformly over the entire circumference of a specific region of the tubular container.

As shown in FIG. 4, the bounce part 14 in this embodiment is a columnar part having a bounce surface 14*a* at the proximal end. The outside diameter of the columnar part is not particularly limited, but in this embodiment it is selected to be equal to the outside diameter of the cylindrical body 13.

The outside diameter of the columnar part forming the bounce part 14 is preferably equal to or greater than the outside diameter of the cylindrical body 13. Thus, the chemical aerosol can be more effectively bounced off, for example, in the direction of the arrow B in FIG. 1(*b*). In addition, when the outside diameter of the cylindrical body 13 is equal to that of the columnar part forming the bounce part 14, the spraying direction changing member 12 is a substantially columnar or cylindrical member having the same diameter as a whole, so that it can be easily handled.

As shown in FIG. 1(*b*), the proximal end surfaces defining the openings 13*c* and 13*c* are opposed to the bounce surface 14*a*. These proximal end surfaces form a second bounce part 13*e* for re-bouncing part of the chemical aerosol bounced back from the bounce surface 14*a*. As shown in FIG. 2, the end surface 7*a* of the outer tube 7 located toward the openings also forms the second bounce part 13*e* together with the proximal end surfaces of the openings 13*c* and 13*c*. Specifically, as shown by the arrow C in FIG. 1(*b*), part of the chemical aerosol hitting and bounced back from the bounce surface 14*a* of the bounce part 14 hits the second bounce part 13*e* and is bounced off in a direction intersecting the direction of the arrow A. The second bounce part 13*e* may be formed to extend outward beyond the outside diameter of the cylindrical body 13. In this case, a flange for forming the second bounce part may be provided integrally with the cylindrical body 13 to continue to the cylindrical body 13.

The second bounce part also has a bounce surface, like the previously-described bounce part. As shown in FIGS. 1(*b*) and 4, the bounce surface of the second bounce part 13*e* in this embodiment is a flat surface opposed to the bounce surface 14*a*. The bounce surface of the second bounce part 13*e*, like the bounce surface of the previously-described bounce part, is not limited to a flat surface and may be a convex conical surface, a concave conical surface or other surfaces. In other words, the bounce surface of the second bounce part is a surface which, when a first straight line beginning at an arbitrary point and extending in one direction is rotated 360 degrees around an axis of rotation which is a second straight line beginning at the arbitrary point and not parallel with the first straight line, is formed by the first straight line.

The bounce surface of the second bounce part may also be a surface formed by rotating, instead of the first straight line, a curved line projecting upward or downward.

Alternatively, the bounce surface of the second bounce part may also be a surface formed by rotating a curved line consisting of an appropriate combination of a concave surface and a convex surface between the center and the outer peripheral edge of the bounce surface in the above manner, so long as it does not have an adverse effect on the chemical coating performance.

The angle formed between the second straight line and the first straight line is preferably 45 to 135 degrees, and within this range, the chemical aerosol having hit the second bounce part can be coated more collectively on a specific region of the tubular container.

The second bounce part should preferably be formed but may not necessarily be formed.

As shown in FIGS. 1(*a*), 1(*b*), 4(*a*), and 4(*b*), the spraying direction changing member 12 in this embodiment is connected at the opening 13*a* side of the cylindrical body 13 to the spray nozzle 4, so that the chemical aerosol can be sprayed from the spray nozzle 4 to the spraying direction changing member 12. The chemical aerosol is sprayed randomly from the spray nozzle 4, but the coating apparatus 10 sprays it outward only through the openings 13*c* because of the existence of the spraying direction changing member 12. The chemical aerosol having hit the bounce surface 14*a* of the bounce part 14 is changed in its direction of spray by the bounce surface 14*a* and thereby sprayed outward through the openings 13*c* and 13*c*. For example, as shown in FIG. 1(*b*), the chemical aerosol having been sprayed from the spray nozzle 4 toward the openings 13*c* is sprayed directly outward through the openings 13*c*, and the chemical aerosol having been sprayed from the spray nozzle 4 toward the bounce part 14 and having hit the bounce surface 14*a* is bounced off as shown by the arrow B and then sprayed outward through the openings 13*c*. Furthermore, the chemical aerosol having been sprayed from the spray nozzle 4 toward the bounce part 14, having hit the bounce surface 14*a* and then having hit the bounce surface of the second bounce part is bounced off as shown by the arrow C and then sprayed outward through the openings 13*c*. In this manner, the chemical aerosol is collected to a region located outside of the region where the openings 13*c* are provided. Therefore, as seen from the usage described later, the chemical solution can be coated only on a specific region of the inside surface of the tubular container.

The coating apparatus 10 changes the direction of spray of the chemical aerosol sprayed from the spray nozzle 4 by means of the spraying direction changing member 12, so that the chemical aerosol is sprayed from the coating apparatus 10 toward a region located radially outward of the portion of the cylindrical body 13 provided with the openings 13*c*. Therefore, the chemical solution can be coated on a specific region of the inside surface of the tubular container.

The bounce part 14 is provided for the purpose of preventing the chemical aerosol from being sprayed from the coating apparatus 10 ahead of the spraying direction changing member 12. Therefore, the bounce surface 14*a* is preferably a surface orthogonal to the direction indicated by the arrow A in FIG. 1(*b*), but it may not necessarily be a surface orthogonal to the direction indicated by the arrow A and need only be a surface intersecting the direction indicated by the arrow A.

Preferably, it is desired that, as in a modification shown in FIG. 7(*a*), an annular projecting wall 14*b* be provided on the outside of the bounce surface 14*a* in FIG. 4(*b*). The provision of the annular projecting wall 14*b* enables the chemical aerosol to be more effectively prevented from being sprayed from the coating apparatus 10 beyond the bounce part 14. The annular projecting wall 14*b* may not necessarily be provided.

Figure 15:
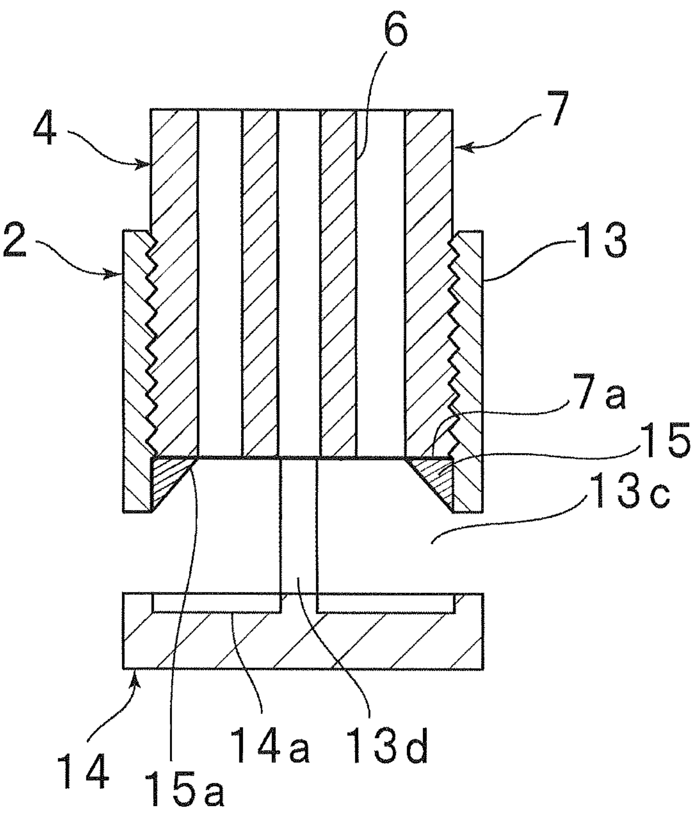
FIG. 15 is a cross-sectional front view schematically showing a spraying direction changing member used in Example 6 of the present invention.

FIG. 15 is a cross-sectional front view showing an essential part of a coating apparatus according to an embodiment of Example 6 of the present invention. In this embodiment, a second bounce member 15 is provided on the end surface 7*a* of the outer tube 7 located towards the openings. The second bounce member 15 is formed of a substantially annular member. The second bounce member 15 may be formed integrally with the outer tube 7 or may be formed of a separate member from the outer tube 7 and fixedly attached to the distal end of the outer tube 7. The inner periphery (bounce surface 15*a*) of the second bounce member 15 is tapered so that its opening diameter decreases as it goes from its distal end to the outer tube 7. Thus, part of the chemical aerosol having been bounced back from the bounce surface 14*a* and having reached the bounce surface 15*a* is bounced again and guided to the openings 13*c*. In this manner, the second bounce member 15 may be provided on the end surface 7*a* of the outer tube 7 in order to form the second bounce surface.

In this embodiment shown in FIG. 15, since the second bounce member 15 is provided, the internal threads provided on the inner periphery of the spraying direction changing member are preferably disposed above and away from the openings 13*c* by a vertical dimension of the second bounce member 15. Thus, as shown in FIG. 15, when the spraying direction changing member 12 is screwed onto the outer tube 7, the second bounce member 15 can be reliably positioned above the openings 13*c*.

The angle of tilt of the second bounce surface 15*a* of the second bounce member 15, i.e., the angle which the bounce surface 15*a* makes with the end surface 7*a* of the outer tube 7 in cross-sectional front view in FIG. 15, is preferably within the range of 20 to 70 degrees. In other words, when the second bounce member 15 is provided on the end surface 7*a* of the outer tube 7, the angle of tilt is preferably within the range of 20 to 70 degrees.

Although in FIG. 15 the second bounce member 15 is provided integrally with the end surface 7*a* of the outer tube 7, the second bounce member may be provided on, out of the end surfaces of the spraying direction changing member 12 surrounding the openings 13*c*, the upper end surface thereof.

The second bounce surface 15*a* of the second bounce member 15, like the previously-described bounce surface 14*a*, may be a curved surface upwardly concave or downwardly convex from inside to outside in cross-sectional front view. Alternatively, the bounce surface 15*a* of the second bounce part may also be a surface formed by rotating a curved line consisting of an appropriate combination of a concave surface and a convex surface between the center and the outer peripheral edge of the bounce surface in the above manner, so long as it does not have an adverse effect on the chemical coating performance.

As is evident from the above-described embodiments and modification, the bounce surface 14*a* in the present invention may be a flat surface or a curved surface, so long as it extends in a direction intersecting the direction of advance of the chemical aerosol. The intersecting direction is preferably a direction orthogonal to the direction of squirt of the chemical aerosol, but it may differ some degrees, for example, ±45 degrees, from the direction orthogonal to the direction of squirt. Furthermore, when the bounce surface 14*a* is a curved surface, it may be a convex curved surface projecting toward the spray nozzle 4 or may be a concave curved surface. Alternatively, the bounce surface 14*a* may also be a surface formed by rotating a curved line consisting of an appropriate combination of a concave surface and a convex surface between the center and the outer peripheral edge of the bounce surface in the above manner, so long as it does not have an adverse effect on the chemical coating performance.

The coating apparatus according to the present invention can be used to coat various liquid substances on specific regions of the inside surfaces of various tubular containers, but it is preferably used to coat a chemical solution on the inside surface of a tubular blood testing container. For example, in some types of blood testing containers, it may be desirable that a chemical solution be deposited above blood to be collected. If, for example, a blood coagulation promoter is previously coated on the inside surface of a blood testing container above the level of blood which will be collected, it is less likely that at the stage of blood collection the blood coagulation promoter will come into contact with the blood. More specifically, during blood collection, bubbles may form in the blood. If the blood is coagulated with bubbles contained therein, subsequent centrifugation may not lead to success. If just after the blood collection the blood does not come into contact with the blood coagulation promoter, it can be avoided that the blood will immediately coagulate with bubbles remaining formed therein. When after the vanishment of bubbles from the blood the blood testing container is turned upside down for mixing to bring the blood into contact with the blood coagulation promoter, the blood can be coagulated with no bubble in the blood. Thus, the accuracy of a test value, such as in a serological test, can be increased. In addition, when the blood coagulation promoter is coated on the blood testing container, sol containing the blood coagulation promoter is less likely to splash over the surrounding area, which provides efficient coating of the blood coagulation promoter and reduces the cost.

The coating apparatus according to the present invention is useful not only in the case of coating a liquid substance on an upper region of the inside surface of a blood testing container as described above but also, for example, in the case of coating a liquid substance on a lower region of the inside surface of a blood testing container. For example, in a blood testing container containing a blood anticoagulant, the blood anticoagulant should desirably be contained in the bottom of the blood testing container. The stream of blood during blood collection allows the anticoagulant contained in the bottom to be uniformly dissolved in the blood for a short period of time. Thus, partial coagulation of the blood can be prevented. With the use of the coating apparatus according to the present invention, a liquid substance can be coated on a specific region of a tubular container, such as a blood testing container, and therefore the blood anticoagulant can also be contained in the blood testing container by coating it only on the bottom surface of the blood testing container.

Example 1

The system shown in FIG. 1 containing the coating apparatus shown in FIGS. 1 and 4 was used.

A spray nozzle was prepared in which an inner tube 6 (with a length of 140 mm, an outside diameter of 0.82 mm, and an inside diameter of 0.41 mm) was inserted in an outer tube 7 (with a length of 81.4 mm, an outside diameter of 3.5 mm, and an inside diameter of 1.0 mm) and the distal end of the inner tube projects 0.1 mm beyond the distal end of the outer tube. The spraying direction changing member 12 described below was attached to the tip of the spray nozzle.

The spraying direction changing member 12 shown in FIG. 7(*a*) was prepared as a stainless steel product. The cylindrical body 13 was 4.5 mm in outside diameter, 3.15 mm in inside diameter, and 10.0 mm in length, and the bounce part 14 was 4.5 mm in outside diameter and 2.5 mm in thickness, i.e., thickness in the direction connecting the proximal and distal ends. The bounce surface 14*a* was a circular surface of 3.15 mm diameter provided at a depth of 0.1 mm from the top surface of the bounce part 14. In other words, the bounce surface 14*a* was the bottom of a recess provided in the top surface of the bounce part 14. Therefore, an annular rising part with a thickness, or a radial dimension, of 0.67 mm was formed on the outside of the recess formed with the bounce surface 14*a*, and the top surface of the annular rising part formed the lower opening end surfaces of the openings 13*c*. The height H of the openings 13*c* was 2 mm and the width of the connecting parts 13*d* and 13*d* was 1.0 mm. The angle α was 90 degrees.

Figure 6:
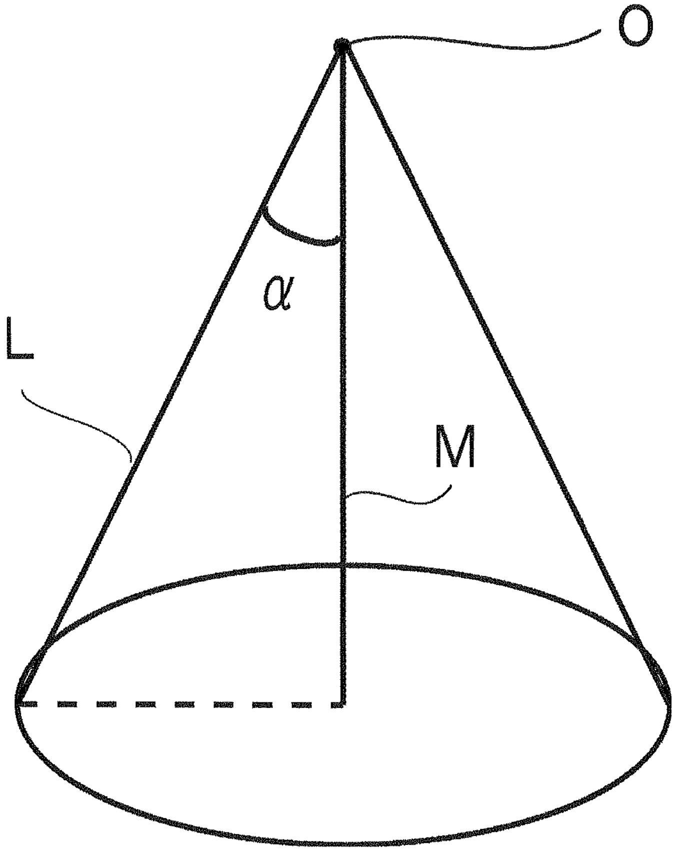
FIG. 6 is a schematic view for illustrating a surface of a bounce part.
Figure 7:
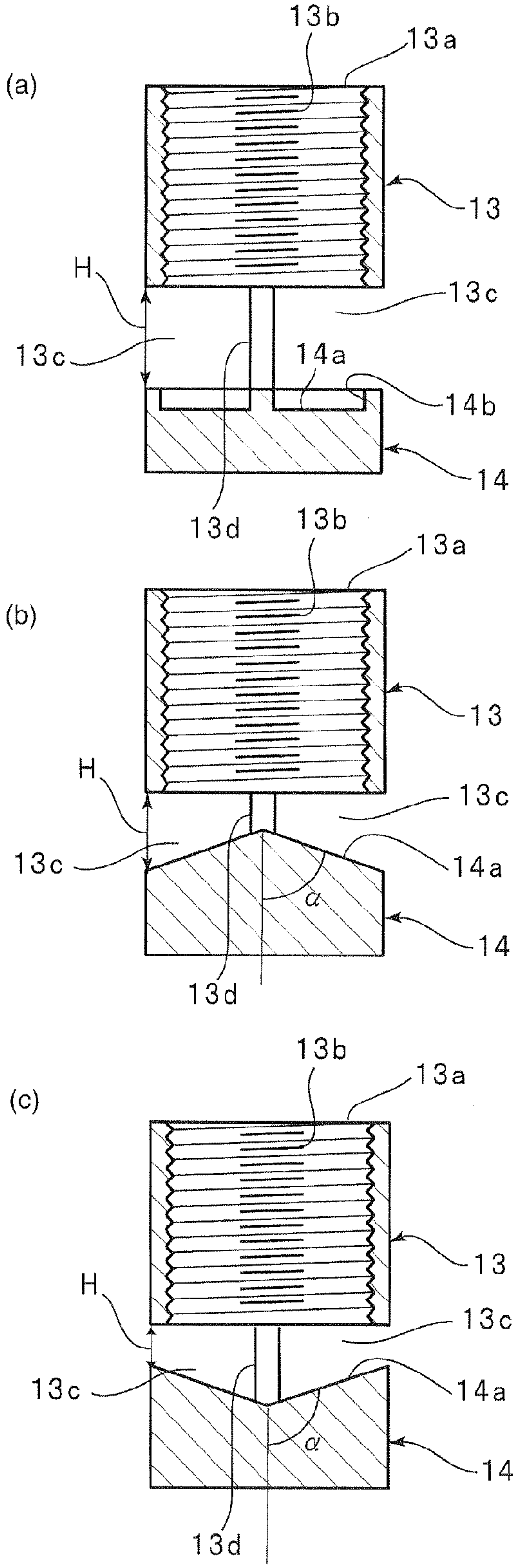
FIG. 7(*a*) is a cross-sectional front view schematically showing a modification of a spraying direction changing member, and FIGS. 7(*b*) and 7(*c*) are cross-sectional front views schematically showing respective spraying direction changing members used in Examples 2 and 3.

The bounce surface 14*a* is a surface having an angle α of 90 degrees made between the first straight line L and the second straight line M in FIG. 6. Therefore, the spraying direction changing member 12 used is the spraying direction changing member 12, shown in FIG. 7(*a*), having a bounce surface 14*a* with an angle α of 90 degrees.

A solution of blood coagulation promoter was prepared in which thrombin, β-alanine, and polyvinylpyrrolidone with a weight-average molecular weight of 45000 (Product Number: K30, manufactured by Wako Pure Chemical Industries, Ltd.) were dissolved in distilled water to give the following respective concentrations.

Thrombin concentration: 12500 units/mL, β-alanine concentration: 5.8% by weight, polyvinylpyrrolidone concentration: 0.8% by weight The above solution of blood coagulation promoter was contained in the chemical solution tank 2 and compressed by air to reach a pressure of 0.24 MPa.

Using the coating apparatus, the solution of blood coagulation promoter was deposited on the inside of a bottomed, tubular blood testing container made of polyethylene terephthalate (with a length of 100 mm, an outside diameter of 13 mm, and an inside diameter of 11 mm) over a region thereof having a width, or a depthwise dimension, of 7 mm centered at a depth of 13 mm from the open end. The weight of the solution of blood coagulation promoter coated was 3.5 mg. Thereafter, air was supplied into the blood testing container to dry the solution of blood coagulation promoter, thereby obtaining a blood testing container coated with the blood coagulation promoter.

Example 2

A coating apparatus was configured in the same manner as in Example 1 except that the angle α in the spraying direction changing member was 80 degrees as shown in FIG. 7(*b*), and a blood testing container coated with a blood coagulation promoter was obtained in the same manner as in Example 1.

Example 3

A coating apparatus was configured in the same manner as in Example 1 except that the angle α in the spraying direction changing member was 100 degrees as shown in FIG. 7(*c*), and a blood testing container coated with a blood coagulation promoter was obtained in the same manner as in Example 1.

Example 4

A coating apparatus was configured in the same manner as in Example 1 except that the angle α in the spraying direction changing member was 45 degrees as shown in FIG. 8(*a*), and a blood testing container coated with a blood coagulation promoter was obtained in the same manner as in Example 1.

Example 5

A coating apparatus was configured in the same manner as in Example 1 except that the angle α in the spraying direction changing member was 135 degrees as shown in FIG. 8(*b*), and a blood testing container coated with a blood coagulation promoter was obtained in the same manner as in Example 1.

Example 6

The spraying direction changing member shown in a cross-sectional front view in FIG. 15 was used as a spraying direction changing member. The angle made between the second straight line and the first straight line in the second bounce surface was 45 degrees. This spraying direction changing member was configured substantially in the same manner as in the modification shown in FIG. 7(*a*) and provided with a second bounce surface shown in FIG. 15. The spraying direction changing member 12 was formed by processing stainless steel like Example 1. The outside diameter, inside diameter, and length of the cylindrical body 13 were equal to those in Example 1. The bounce part 14 was 4.5 mm in outside diameter and 2.5 mm in thickness. The bounce surface 14*a* was a circular surface of 3.15 mm diameter provided at a depth of 0.1 mm from the top surface of the bounce part 14. In other words, the bounce surface 14*a* was the bottom of a recess provided in the top surface of the bounce part 14. Therefore, an annular rising part with a thickness, or a radial dimension, of 0.67 mm was formed on the outside of the recess formed with the bounce surface 14*a*, and the top surface of the annular rising part formed the lower opening end surfaces of the openings 13*c*. The height of the openings 13*c* was 1 mm. The angle α was 90 degrees.

A coating apparatus was configured for the rest in the same manner as in Example 1, and a blood testing container coated with a blood coagulation promoter was obtained in the same manner as in Example 1.

Comparative Example

Without the use of a spraying direction changing member and with the use of only a spray nozzle prepared in Example 1, a solution of blood coagulation promoter was coated on the inside surface of a blood testing container in an attempt for the coating region to be centered at a depth of 13 mm from the open end of the blood testing container. Thereafter, air was supplied into the blood testing container to dry the solution of blood coagulation promoter, thereby obtaining a blood testing container coated with the blood coagulation promoter.

Evaluation of Examples and Comparative Example

Figure 11:
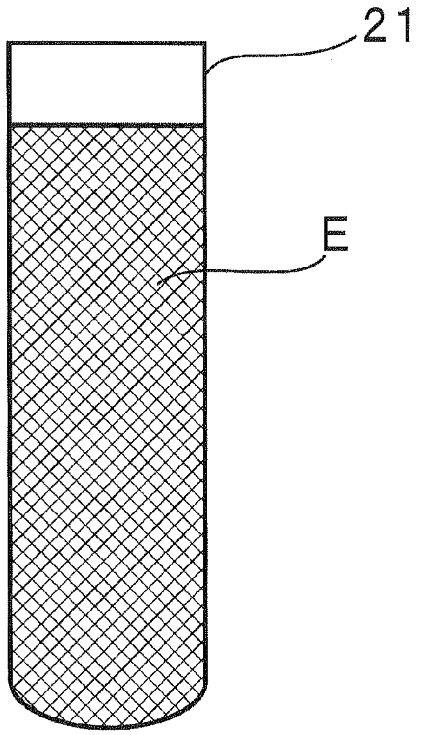
FIG. 11 is a cross-sectional front view schematically showing a state that a blood coagulation promoter is coated on the inside surface of a tubular container in a comparative example.

For Examples 1 to 6 and the comparative example, the portions of the blood testing containers coated with blood coagulation promoter were visually observed after drying. As a result, in the comparative example, the entire inside surface of the blood testing container 21 was coated with the blood coagulation promoter as shown in FIG. 11, so that the width of coating could not be controlled.

In contrast, in Examples 1 to 6, the blood coagulation promoter was coated on an annular region of a certain constant width of the blood testing container, the region being centered at a depth of 13 mm from the open end of the blood testing container. In Examples 4 and 5 the widths of coating were as relatively wide as 50 mm and 30 mm, respectively, while in Examples 2 and 3 the widths of coating could be as narrow as 20 mm and 10 mm, respectively. Furthermore, in Example 1, the blood coagulation promoter could be coated, as shown in FIG. 10, on an annular region D of the blood testing container 21 with a width of coating of 7 mm. The reason for this is that since the angle α in the spraying direction changing member was 90 degrees, the chemical aerosol from the spray nozzle could be uniformly bounced off from the bounce surface of the bounce part.

Moreover, in Example 6, since the "second bounce part" was provided and the height of the openings 13*c* was 1 mm, the blood coagulation promoter could be coated on an annular region D of the blood testing container 21 with a width of coating of 5 mm.

Figure 12:
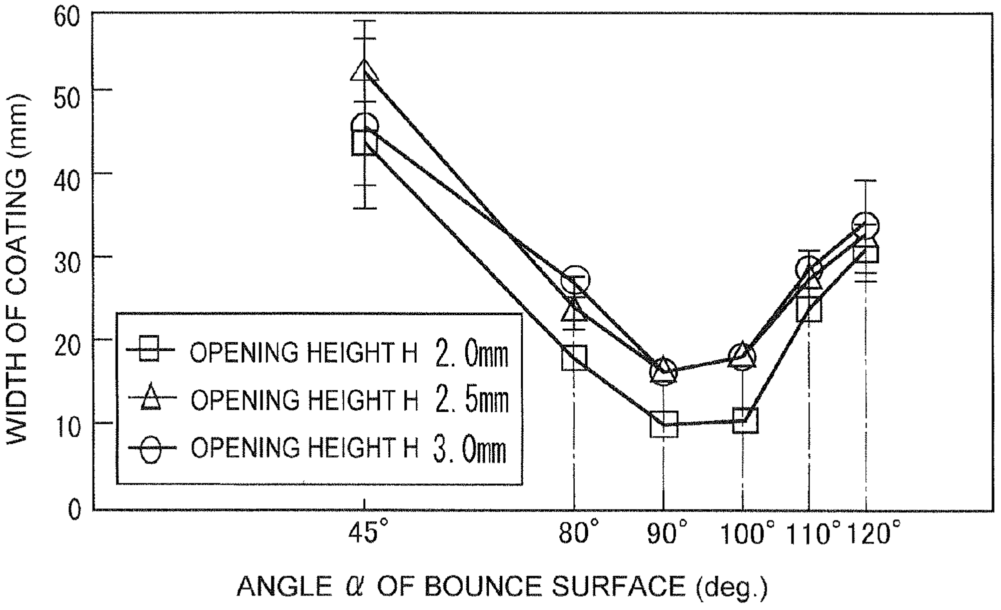
FIG. 12 is a graph showing the relationship between the angle α of a bounce surface of a bounce part of the spraying direction changing member and the width of coating.

Next, the coating apparatus used in Example 1 was altered into various modifications by varying the height (dimension H in FIG. 4(*b*)) of its opening 13*c* and the angle α of its spraying direction changing member. For each modification, a blood coagulation promoter was coated on the inside surface of a blood testing container in the same manner as in Example 1, and the width of coating was measured in the same manner as in Example 1. The results are shown in FIG. 12. In FIG. 12, the abscissa axis represents the angle α of the flat surface of the bounce plate, and the ordinate axis represents the width of coating.

As is evident from FIG. 12, even when the opening height H (see FIG. 4(*b*)) of the opening 13*c* is any of 2.0 mm, 2.5 mm, and 3.0 mm, there is the same tendency. Specifically, FIG. 12 shows that when the angle α of the bounce part 14 is within the range of 45 to 120 degrees, the width of coating can be approximately 50 mm or less, and that more preferably when the angle α is within the range of 80 to 110 degrees, the width of coating can be approximately 30 mm or less. FIG. 12 also shows that still more preferably when the angle α is within the range of 90 to 100 degrees, the width of coating can be approximately 20 mm or less. It is also shown that also considering that the width of coating was 30 mm in Example 5 in which the angle α was 135 degrees, the width of coating can be approximately 50 mm or less when the angle α of the bounce part 14 is within the range of 45 to 135 degrees.

REFERENCE SIGNS LIST

1 . . . System
2 . . . Chemical solution tank
3 . . . Pipe
4 . . . Spray nozzle
5 . . . Pump
6 . . . Inner tube
6*a* . . . Opening
6*b* . . . Discharge opening
7 . . . Outer tube
8 . . . Space
9 . . . Opening
10 . . . Coating apparatus
11 . . . Compressor
12 . . . Spraying direction changing member
13 . . . Cylindrical body
13*a* . . . Opening
13*b* . . . Internal threads
13*c* . . . Opening
13*d* . . . Connecting part
13*e* . . . Second bounce part
13*f* . . . Distal end of cylindrical body 13
14 . . . Bounce part
14*a* . . . Bounce surface
14*b* . . . Annular projecting wall
15 . . . Second bounce member
15*a* . . . Bounce surface
20 . . . Centering structure
21 . . . Tubular container
31 . . . Pipe

The invention claimed is:

1. A coating apparatus for coating a liquid substance on a specific region of the inside surface of a tubular container, the coating apparatus comprising:

a spray nozzle including an inner tube for discharging the liquid substance and an outer tube with the inner tube inserted therein for discharging, a medium exhibiting fluidity, the spray nozzle being configured to spray from a tip thereof the liquid substance discharged from the inner tube as an aerosol by means of the medium discharged from the outer tube; and a spraying direction changing member, fixed to a tip side of the spray nozzle, for changing a direction of spray of the aerosol oriented outward to a direction intersecting a direction of discharge of the liquid substance, wherein the spraying direction changing member further includes a first bounce part provided, to directly face the outlet of the inner tube and the outlet of the outer tube of the spray nozzle, the first bounce part having a bounce surface for bouncing off the aerosol discharged from the spray nozzle.

2. The coating apparatus according to claim 1, wherein the spraying direction changing member further includes a cylindrical body with a hollow part extending from the tip of the spray nozzle in the direction of discharge of the liquid substance, the sidewall of the cylindrical body has openings formed to pass through the sidewall in a direction intersecting the direction of discharge of the liquid substance from the inner tube, and the aerosol is sprayed outward through the openings.

3. The coating apparatus according to claim 2, wherein the first bounce part is provided on the side beyond the openings of and at the distal end of the cylindrical body.

4. The coating apparatus according to claim 3, wherein the bounce surface is a fiat surface.

5. The coating apparatus according to claim 3, wherein the bounce surface is a convex surface projecting toward the spray nozzle or a concave surface whose deepest part is located on the side opposite to the spray nozzle.

6. The coating apparatus according to claim 3, wherein the bounce surface is a surface which, when a first straight line beginning at an arbitrary point and extending in one direction is rotated 360 degrees around an axis of rotation which is a second straight line beginning at the arbitrary point and not parallel with the first straight line, is formed by the first straight line.

7. The coating apparatus according to claim 6, wherein the angle firmed between the first straight line and the second straight line is within the range of 45 to 135 degrees.

8. The coating apparatus according to claim 7, wherein the angle is 90 degrees.

9. The coating apparatus according to claim 8, wherein the first straight line is provided to be orthogonal to the direction of discharge of the liquid substance.

10. The coating apparatus according to claim 9, wherein the inner tube has a distal end opening in the shape of a circle and the second straight line is a straight line extending from the center of the circle in the direction of discharge of the liquid substance.

11. The coating apparatus according to claim 6, wherein the inner tube has a distal end opening in the shape of a circle and the second straight line is a straight line extending from the center of the circle in the direction of discharge of the liquid substance.

12. The coating apparatus according to claim 7, wherein the inner tube has a distal end opening in the shape of a circle and the second straight line is a straight line extending from the center of the circle in the direction of discharge of the liquid substance.

13. The coating apparatus according to claim 1, further comprising a second bounce part provided on the tip side of the spray nozzle and outward of a part of the spray nozzle from which the medium exhibiting fluidity is discharged, the second bounce part being opposed to the first bounce part of the spraying direction changing member, wherein the second bounce part has a bounce surface formed to re-bounce the aerosol bounced back from the bounce surface of the first bounce part of the spraying direction changing member and spray the aerosol outward.

14. The coating apparatus according to claim 13, wherein the second bounce part has a surface which, when a first straight line beginning at an arbitrary point and extending in one direction is rotated 360 degrees around an axis of rotation which is a second straight line beginning at the arbitrary point and having an angle of 45 to 135 degrees made with the first straight line, is formed by the first straight line.

15. The coating apparatus according to claim 13, wherein the medium exhibiting fluidity is a gas.

16. The coating apparatus according to claim 1, wherein the medium exhibiting fluidity is a gas.

17. The coating apparatus according to claim 1, wherein the tubular container is a blood testing container.

18. The coating apparatus according to claim 13, wherein the tubular container is a blood testing container.

19. A method for coating a liquid substance on a specific region of the inside surface of a tubular container, the method comprising the steps of:

positioning the coating apparatus according to claim 1 in the tubular container so that a direction of spray of an aerosol oriented outward is turned toward the specific region of the tubular container; and coating the aerosol on the specific region of the container by discharging the liquid substance from the inner tube of the spray nozzle of the coating apparatus and a medium exhibiting fluidity from the outer tube of the spray nozzle to thereby spray the aerosol from the spray nozzle and changing the direction of spray of the aerosol oriented outward to a direction intersecting, a direction of discharge of the liquid substance from the inner tube of the spray nozzle by means of the spraying direction changing member of the coating apparatus.

20. The liquid substance coating method according to claim 19, wherein the spraying direction changing member includes a cylindrical body with a hollow part extending from the tip of the spray nozzle in the direction of discharge of the liquid substance and closed at its distal end of the hollow part, the sidewall of the cylindrical body has openings formed to pass through the sidewall in a direction intersecting the direction of discharge of the liquid substance from the inner tube, and the aerosol is sprayed outward through the openings.

21. The liquid substance coating method according to claim 20, wherein the medium exhibiting fluidity is a gas, and the tubular container is a blood testing container.

* * * * *